(12) United States Patent
You et al.

(10) Patent No.: US 8,802,893 B2
(45) Date of Patent: Aug. 12, 2014

(54) METHOD OF ACCELERATING METHANOL CARBONYLATION

(75) Inventors: Zhixiong You, Yokohama (JP); Takeshi Minami, Yokohama (JP); Chunji Yin, Yokohama (JP); Yoichi Umehara, Yokohama (JP); Tetsuro Matsumura, Yokohama (JP); Chikako Hashimoto, Yokohama (JP); Yasuo Hosono, Yokohama (JP)

(73) Assignee: Chiyoda Corporation, Yokohama-shi (JP)

( * ) Notice: Subject to any disclaimer, the term of this patent is extended or adjusted under 35 U.S.C. 154(b) by 63 days.

(21) Appl. No.: 13/257,379

(22) PCT Filed: Feb. 8, 2011

(86) PCT No.: PCT/JP2011/000676
§ 371 (c)(1),
(2), (4) Date: Sep. 19, 2011

(87) PCT Pub. No.: WO2011/099264
PCT Pub. Date: Aug. 18, 2011

(65) Prior Publication Data
US 2012/0010371 A1 Jan. 12, 2012

(30) Foreign Application Priority Data
Feb. 9, 2010 (JP) ................................. 2010-026293

(51) Int. Cl.
*C07C 51/10* (2006.01)
(52) U.S. Cl.
USPC ...................... 562/519; 525/327.1; 525/331.9; 525/333.3; 525/328.5; 525/343; 525/344; 525/353; 525/370; 562/400; 562/512; 502/326; 502/402

(58) Field of Classification Search
USPC ............. 525/327.1, 331.9, 333.3, 328.5, 343, 525/344, 353, 370; 562/400, 512, 519
See application file for complete search history.

(56) References Cited

U.S. PATENT DOCUMENTS 4,100,359 A * 7/1978 Schmerling et al. .......... 560/232
(Continued)

FOREIGN PATENT DOCUMENTS

JP 47-003334 U 2/1972
(Continued)

OTHER PUBLICATIONS

International Search Report of PCT/JP2011/000676, mailing date Mar. 8, 2011.
Shimazu, Shogo et al., "Methanol Carbonylation Catalyzed by Polymer-Supported Rhodium Complexes", Applied Catalysis, 1987, pp. 279-288, vol. 35.

(Continued)

*Primary Examiner* — Robert C Boyle
(74) *Attorney, Agent, or Firm* — Westerman, Hattori, Daniels & Adrian, LLP (57) ABSTRACT

According to a method for producing acetic acid by carbonylation of methanol characterized in that an acid having an acid dissociation constant ($pK_a$) smaller than the constant of acetic acid is allowed to be present in the reaction system, acetic acid can be produced by the reaction of methanol and carbon monoxide in a reaction liquid in the presence of a solid catalyst containing rhodium and alkyl iodide, to achieve an enhanced reaction rate of carbonylation of methanol in producing acetic acid in the region at a high carbonylation degree ($Ca>0.8$ mol/mol) for more efficient production of acetic acid.

4 Claims, 4 Drawing Sheets (56) References Cited

U.S. PATENT DOCUMENTS

| | | | | |
|---|---|---|---|---|
| 4,295,952 | A | * | 10/1981 | de Nora et al. ............... 204/252 |
| 5,334,755 | A | * | 8/1994 | Yoneda et al. ................. 562/519 |
| 5,679,837 | A | * | 10/1997 | Shinoda ........................ 560/239 |
| 6,235,673 | B1 | | 5/2001 | Zoeller et al. |
| 6,420,304 | B1 | * | 7/2002 | Tsai et al. ..................... 502/207 |
| 2008/0269519 | A1 | | 10/2008 | Miller et al. |

FOREIGN PATENT DOCUMENTS

| | | |
|---|---|---|
| JP | 63-253047 A | 10/1988 |
| JP | 5-306253 A | 11/1993 |
| JP | 5-306254 A | 11/1993 |
| JP | 6-315637 A | 11/1994 |
| JP | 6-345680 A | 12/1994 |
| JP | 2003-530218 A | 10/2003 |
| JP | 2008-524179 A | 7/2008 |
| WO | 01/77053 A2 | 10/2001 |
| WO | 2006/064178 A1 | 6/2006 |

OTHER PUBLICATIONS

International Preliminary Report on Patentability, mailing date of Aug. 23, 2012, International Application No. PCT/JP2011/000676.
Howard et al., "C1 to acetyls: catalysis and process", Catalysis Today, vol. 18, 1993, pp. 325-354.
Sunley et al., "High Productivity methanol carbonylation catalysis using iridium The CativaTM process for the manufacture of acetic acid", Catalysis Today, vol. 58, 2000, pp. 293-307.
Blasio et al., "Activity and Stability of Two Polymer-Supported Rhodium-Based Catalysis for the Vapour Phase Carbonylation of Methanol", Journal of Catalysis, vol. 176, 1998, pp. 253-259.
Hjortkjaer et al., "Rhodium Complex Catalyzed Methanol Carbonylation. Effects of Medium and Various Additives", Ind. Eng. Chem. Prod. Res. Dev., vol. 16, pp. 281-285, published Dec. 1977.
Fulford et al., "Factors influencing the oxidative addition of iodomethane to [Rh(CO)2I2]-, the key step in methanol and methyl acetate carbonylation", Journal of Organometallic Chemistry, vol. 398, 1990, pp. 311-323.

* cited by examiner

SYNTHESIS EXAMPLE 1

FIG. 2B

SYNTHESIS EXAMPLE 2

METHOD OF ACCELERATING METHANOL CARBONYLATION

TECHNICAL FIELD

The present invention relates to a method for enhancing reaction rate in producing acetic acid by carbonylation of methanol.

BACKGROUND ART

Acetic acid is a basic chemical product having a wide range of uses such as raw material for poly vinyl acetate, acetylcellulose and ester acetates, solvent in manufacturing plant for terephthalic acid, and the like.

Known methods for producing acetic acid used in chemical industry include carbonylation of methanol, partial oxidation of acetaldehyde, and oxidation of butane or propane. Presently, carbonylation of methanol is performed for the most part thereof.

As a method for producing acetic acid by carbonylation of methanol, "Monsanto process" (Patent Literature 1) using the reaction of methanol and carbon monoxide in acetic solvent containing water, with rhodium compound and methyl iodide homogeneously dissolved therein, is well known.

Although this method has an advantage in producing acetic acid from methanol with a high yield, there still have existed the following problems associated with the method.

First, coexistence of highly-concentrated water is required to keep a high carbonylation reaction rate and high acetic acid selectivity. The highly-concentrated water accelerates the hydrolysis of methyl iodide which is used as a co-catalyst in this method, and produces a large quantity of hydroiodic acid. The hydroiodic acid corrodes the equipment system. Furthermore, due to the necessity of separation of the water and hydroiodic acid mixed in acetic acid, it increases the load of the refining process for the acetic acid production, which results in high production cost. Second, due to the low solubility of the catalytic metal complex in solvent, a high reaction rate cannot be obtained. And third, the dissolved catalyst precipitates in the steps of separation and refinement, which substantially increases the cost and load for the separation and recovery thereof.

In order to solve these problems, an advanced method that the reaction proceeded in a heterogeneous system having rhodium supported on a pyridine resin carrier (Patent Literatures 2 to 5) has been proposed and put into practical use.

According to these prior arts, firstly, a high carbonylation reaction rate and a high acetic acid selectivity can be kept even under such conditions where reaction system has a lower water concentration of not higher than 5 wt %. Since producing of acetic acid can be done under a lower water concentration condition, the amount of hydroiodic acid produced by the hydrolysis of methyl iodide as a co-catalyst is reduced, resulting in reduced risk of corroding of materials used in the equipment system. In addition, the easiness of separation, recovery, and refinement of the produced acetic acid is enabled, which leads to reduced load in the refining process for the acetic acid production, resulting in an advantage of a lower cost. Secondly, since the rhodium complex is supported, a high concentration of catalyst can be achieved despite the low solubility of the rhodium complex, resulting in an enhanced reaction rate. And thirdly, since the catalyst is contained in the reactor, loss of rhodium can be reduced in the steps of separation and refinement.

According to the Patent Literature 3, preferably the carbonylation reaction of methanol is performed in the region where liquid reaction product has a carbonylation degree Ca of not lower than 0.8 mol/mol.

A carbonylation degree Ca is a value defined by the following expression.

$$Ca = \Sigma_i^n Ci \cdot Zi / \Sigma_i^n Ci \cdot Xi \quad \text{[Expresssion1]}$$

In the expression, Ci represents a molar concentration (mol/l) of each component Mi existing in solution, Zi represents a carbonylation factor of each component Mi, and Xi represents a raw material factor of each component Mi, respectively. And n represents the total number of the components Mi existing in solution. The carbonylation factor Zi and the raw material factor Xi of each component Mi are shown in the following table.

TABLE 1

| Component (Mi) | Carbonylation factor (Zi) | Raw material factor (Xi) |
|---|---|---|
| Methyl iodide | 0 | 0 |
| Methanol | 0 | 1 |
| Acetic acid | 1 | 1 |
| Methyl acetate | 1 | 2 |
| Water | 0 | 0 |
| Dimethyl ether | 0 | 2 |
| Carbon monoxide | 0 | 0 |
| Other organic compound | 0 | 0 |

In the carbonylation reaction of methanol, the main reaction represented by the following reaction formula (1) involves side reactions represented by the following reaction formulae (2) and (3).

$$CH_3OH + CO \longrightarrow CH_3COOH \quad (1)$$

$$CH_3COOH + CH_3OH \longrightarrow CH_3COOCH_3 + H_2O \quad (2)$$

$$2CH_3OH \longrightarrow CH_3OCH_3 + H_2O \quad (3)$$

$$CH_3I + H_2O \longrightarrow CH_3OH + HI \quad (4)$$

The by-product water produced from the side reactions (2) and (3) produces hydroiodic acid by hydrolysis, as shown in (4), of methyl iodide as a co-catalyst, which may corrode the equipment system. And due to the necessity of separation of the by-product water and hydroiodic acid mixed in acetic acid, the load in the refining process for acetic acid production increases, which may further result in a high production cost.

In contrast, performing of reaction in the region at a high carbonylation degree can inhibit the side reactions (2) and (3), and thus reduces the production of hydrogen iodide in (4). In addition, by inhibiting the production of water and methyl acetate as by-products, acetic acid concentration in reaction products can be increased, resulting in an advantage of lower cost for refinement.

CITATION LIST

Patent Literature

PTL 1: Japanese Patent Publication No. S47-3334
PTL 2: Japanese Patent Application Laid-Open No. S63-253047
PLT 3: Japanese Patent Application Laid-Open No. H05-306253
PLT 4: Japanese Patent Application Laid-Open No. H05-306254
PLT 5: Japanese Patent Application Laid-Open No. H06-315637

SUMMARY OF INVENTION

Technical Problem

However, in the preferred range of carbonylation degree (Ca>0.8 mol/mol) according to Patent Literature 3, high reaction rate cannot be maintained and acetic acid cannot be efficiently produced.

Accordingly, it is the object of the present invention to provide a method for producing acetic acid by heterogeneous reaction of methanol and carbon monoxide in a reaction liquid in the presence of a solid catalyst containing rhodium and alkyl iodide, to achieve an enhanced reaction rate in producing acetic acid in the region of a high carbonylation degree (Ca>0.8 mol/mol) for more efficient production of acetic acid.

Solution to Problem

In view of the above object, a method according to the present invention for producing acetic acid by heterogeneous reaction of methanol and carbon monoxide in a reaction liquid in the presence of a solid catalyst containing rhodium and alkyl iodide is provided, which method being characterized in that an acid having an acid dissociation constant ($pK_a$) smaller than the constant of acetic acid, that acid being co-existent with the solid catalyst in the reaction system.

Advantageous Effects of Invention

According to the method described above, the reaction rate of hydrolysis of methyl acetate that is the rate-determining step in producing acetic acid in the range of a high carbonylation degree can be accelerated. This enables enhancement of the reaction rate of the whole system, resulting in more efficient production of acetic acid. In addition, since the amount of methyl acetate accompanying the produced acetic acid is reduced, the load of separation and recovery of acetic acid can be reduced, resulting in a reduced production cost of acetic acid.

Furthermore, as a side effect of the present invention, the carbonylation reaction performed under conditions with a high Ca enables production of acetic acid under low concentrations of methyl acetate and water, and inhibits the decomposition of the vinylpyridine resin used as a carrier in the catalyst. This reduces the load of the equipment for removing the nitrogen-containing decomposition compounds, resulting in prevention of loss of rhodium ionically bonded with nitrogen-containing compounds from the reactor.

BRIEF DESCRIPTION OF DRAWINGS

[FIG. 1]

[FIG. 2A]

[FIG. 2B]

[FIG. 2C]

[FIG. 2D]

[FIG. 3]

[FIG. 4]

DESCRIPTION OF EMBODIMENTS

According to the present invention, a method for producing acetic acid by reaction of methanol and carbon monoxide in a reaction liquid in the presence of a solid catalyst containing rhodium and alkyl iodide is provided, which method enables an enhanced carbonylation reaction rate in the region of a carbonylation degree of not lower than 0.8 mol/mol (hereinafter referred to as the region with a high carbonylation degree), and which method being characterized in that an acid as a catalyst for the hydrolysis of methyl acetate is co-existent with the solid catalyst in the reaction system.

Figure 1:
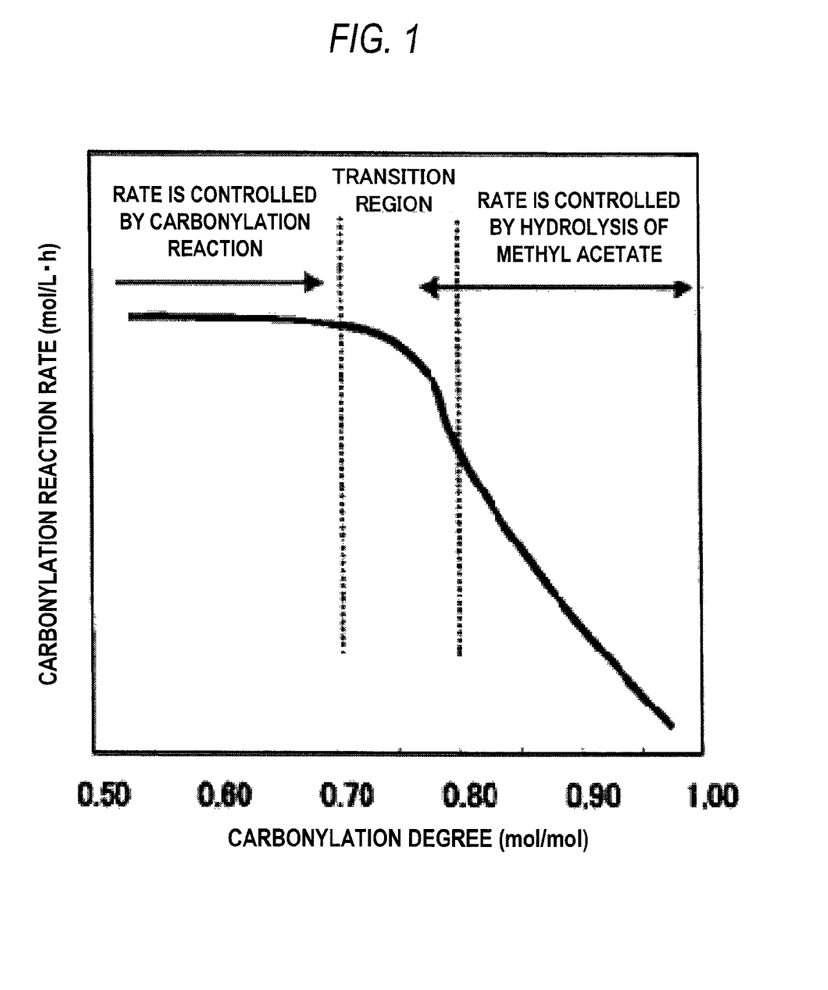
FIG. 1 is a graph illustrating relations between carbonylation degree of liquid reaction product and carbonylation reaction rate.

In the region with a high carbonylation degree, although water as a by-product produced from side reactions of carbonylation can be inhibited, the carbonylation reaction rate is reduced as shown in FIG. 1. Accordingly, production of acetic acid is usually performed at the transition region with a Ca of 0.7 to 0.8. However, since large quantities of methyl acetate and water in a reactor are produced in this region, the effective rate of the reaction system is reduced with increased load of refinement of the product acetic acid, which raises a problem of imposing a higher cost.

As a result of earnest examinations, the present inventors have found that the cause of the lowering of reaction rate in the region at a high carbonylation degree is that the water content existing in the whole system is reduced due to hydrolysis of methyl acetate and the hydrolysis of methyl acetate (the reverse reaction in the reaction formula (2)) becomes the rate-determining step of the reaction system.

Consequently, lowering of reaction rate in the region with a high carbonylation degree can be prevented by addition of a catalyst for accelerating the hydrolysis of methyl acetate, the rate-determining step to the reaction system. In addition, by accelerating the hydrolysis of methyl acetate, necessary load for separating and recovering methyl acetate from acetic acid are reduced, resulting in a higher efficiency and lower cost for the total production process for acetic acid.

It is well known that hydrolysis of ester such as methyl acetate is accelerated by addition of an acid or a base as a catalyst.

Of these, since base reacts with acetic acid, hydrolysis of methyl acetate cannot be accelerated with a base catalyst in the present system. As a result, preferably acid is used as a catalyst, and use of acid having an acid dissociation constant ($pK_a$) smaller than the constant of acetic acid is particularly preferred for acceleration of the hydrolysis with increased concentration of hydrogen ion. Preferably the acid for use has a $pK_a$ of −8 to 4, more preferably −5 to 2.

Examples of the approach to allowing an acid to be co-existent in the reaction system in the present invention include, but not limited to, provision of a resin carrier used in a catalyst for carbonylation reaction with acidic centers and addition of an acid to the reaction liquid.

To provide a resin carrier with acidic centers, for example, an acidic group such as a sulfonic acid group may be introduced to a pyridine resin used for supporting rhodium.

According to the present inventors' knowledge, it is difficult to introduce an acidic group such as a sulfonic group sufficiently to 4-vinylpyridine/divinylbenzene copolymer that is usually used as a rhodium catalyst carrier, without modification. The reasons are believed to be that in the case of 4-vinylpyridine an acid-base reaction occurs between the basic pyridine group and the acid, and in the case of divinylbenzene a group that is substituted to divinylbenzene's para position after polymerization acts as a steric hindrance for sulfonation.

Consequently, in the case of introducing an acidic group to a pyridine resin, preferably a monomer that has no substituent group at a para position to a vinyl group is introduced for copolymerization with pyridine. For example, when styrene is used as the monomer, a sulfonic group as an acidic group can be introduced into styrene's benzene ring. In this regard, the preferred monomer ratios of 4-vinylpyridine, styrene, and divinylbenzene are 5% to 60% by weight of 4-vinylpyridine, 1% to 50% by weight of styrene, and 5% to 40% by weight of divinylbenzene. When the ratio of 4-vinylpyridine is lower than the above, catalytic activity for methanol carbonylation would be insufficient. When the ratio of styrene is lower than the above, since acidic centers would be insufficiently provided, hydrolysis of methyl acetate is not accelerated. When the ratio of divinylbenzene is lower than the above, sufficient degree of cross-linkage would not be produced, and hence sufficient strength of a pyridine resin is not achieved under the high temperature and high pressure conditions where the carbonylation reaction is proceeded. Preferably the 4-vinylpyridine/styrene/divinylbenzene copolymer has a degree of cross-linkage not lower than 10%.

The method for sulfonation may include any known method such as use of a sulfonation agent including concentrated sulfuric acid, chlorosulfonic acid, or sulfuric anhydride.

When the acid is added to the reaction liquid, since the reactions of the system proceed under high temperature and high pressure conditions, use of a volatile acid may cause corrosion of the equipment by the volatilized acid during separation and recovery of acetic acid. Hence, it is preferred to use a nonvolatile acid such as sulfuric acid or an acidic cation-exchange resin for preventing corrosion of the equipment. Furthermore, the use of a nonvolatile acid or an acidic cation-exchange resin enables reuse of the circulated reaction liquid without newly adding the acid, resulting in more efficient production of acetic acid. Of these, it is more preferred to use an acidic cation-exchange resin due to easiness of separation from the reaction liquid.

Although the type of the acidic cation-exchange resin is not specifically limited, it is preferred to use a strong acidic cation-exchange resin for accelerating hydrolysis with a high concentration of hydrogen ion.

In the present invention, either acidic cation-exchange resin of a porous type having macro pores (including any of a porous type, a high porous type, or an MR type) or a gel type having no macro pore may be used. Examples of the strong acidic cation-exchange resin of a porous type include MSC-1, Dowex (manufactured by The Dow Chemical Company), PK-208, PK-212, PK-216, PK-220, PK-228, SK-104 (manufactured by Mitsubishi Chemical Corporation), Amberlyst-15, Amberlyst-16, Amberlyst-35, IR-116, IR-118, IR-122, C-26, C-26TR, C-264, C-265 (manufactured by Rohm and Haas Company), SPC-108, SPC-112 (manufactured by Bayer AG), and KC-470 (manufactured by Sumitomo Chemical Co., Ltd). Examples of the strong acidic cation-exchange resin of a gel type include HCR-S, HCR-W2, HGR-W2 (manufactured by The Dow Chemical Company), SK-1B, SK-106, SK-110 (manufactured by Mitsubishi Chemical Corporation), Duolite C20H, C255LFH, Amberlyst-31 (manufactured by Rohm and Haas Company), K1221, and K1431(manufactured by Bayer AG).

Preferably the acidic cation-exchange resin for use has a degree of cross-linkage of 1% to 60%, more preferably 5% to 50%, and an average particle diameter of 0.1 mm to 10 mm, more preferably 0.25 mm to 0.85 mm.

Preferably the acidic cation-exchange resin is added in the amount of 1 wt % to 30 wt % of the reaction liquid.

The amount of the reaction liquid denotes the amount of the total liquid, such as methanol, alkyl iodide, and water, introduced into the reaction system. Hence, the amount of a solid catalyst such as a rhodium-containing solid catalyst or an acidic cation-exchange resin is not included in the amount of the reaction liquid.

When the resin is added in an amount less than the above range, hydrolysis of methyl acetate is not sufficiently accelerated, and no advantageous effect is obtained. For the meanwhile, when the resin is added in an amount more than the range, fluidity of the reaction liquid is lowered and the relative amount of the reaction liquid is reduced, resulting in a low production efficiency of acetic acid.

Preferably the reaction temperature is in the range of 100° C. to 250° C. in order to prevent thermal decomposition of the resin.

In the present invention, acid is added to the reaction liquid prior to introduction of the reaction liquid to a reactor or to the reaction liquid in a reactor. In the case of circulating the reaction liquid, the acid added to the reaction liquid is also circulated with the reaction liquid for reuse. If needed, acid may be newly added.

Of the approaches to allowing an acid to be co-existent in the reaction system, it is preferred to provide a resin carrier used in the catalyst for carbonylation reaction with acidic centers, because the reaction rate in the region at a high carbonylation degree can be enhanced. The reason is considered as follows.

Carbonylation reaction proceeds in pores of a catalyst having many active sites (rhodium complex). Particularly in the region at a high carbonylation degree, the equilibrium of the reaction formula (2) is shifted to the right side, which leads to a reduced amount of methanol in the entire reaction liquid, and the difference in methanol concentration between of the reaction liquid and in the pores is also reduced. Consequently, since methanol is not supplied from the reaction liquid into the pores, the rate of supplying of methanol to active sites in the pores depends on the rate of hydrolysis of methyl acetate. On the other hand, since the methyl acetate concentration of the reaction liquid is sufficiently high even in the region at a high carbonylation degree, methyl acetate is considered to promptly diffuse from the reaction liquid into the pores. According to the present inventors' knowledge, for example, as shown in Table 2, while the methanol concentration of the reaction liquid significantly differs depending on the carbonylation degree, the methyl acetate concentration is retained at a certain level even at a high carbonylation degree.

TABLE 2

| Carbonylation degree | CH$_3$OH concentration | CH$_3$COOCH$_3$ concentration |
|---|---|---|
| 0.75 mol/mol | 0.9 wt % | 28 wt % |
| 0.85 mol/mol | 0.2 wt % | 15 wt % |

When carbonylation reaction proceeds, methanol is further consumed. As a result, methanol produced by hydrolysis of methyl acetate will have a greater effect on the carbonylation reaction rate. On this occasion, since acidic centers provided adjacent to active sites (rhodium complex) of the carbonylation reaction accelerate hydrolysis of methyl acetate in pores, the produced methanol may be efficiently supplied to the carbonylation reaction. Consequently, the carbonylation reaction rate is also efficiently enhanced.

EXAMPLES

In Example 1, effects of the presence of the acid in the reaction system on the carbonylation reaction rate were studied. In Examples 2 to 4, effects of the presence of the acid in the reaction liquid under various conditions were studied.

Example 1

In this example, the change in carbonylation reaction rate by sulfonated pyridine resins polymerized by adding styrene (Synthesis examples 1 to 3) were investigated, to study the effects of acidic centers provided in styrene resins. In addition, for a pyridine resin prepared by a conventional method (Synthesis example 4), the effects of acidic centers provided in the reaction liquid using a cation-exchange resin were also studied.

Synthesis Example 1

[Preparation of the Resin]

The resin is prepared by a suspension polymerization method, in which as an aqueous phase, 10 wt % of sodium chloride, 0.3 wt % of sodium nitrite, 0.064 wt % of gelatin, and 0.009 wt % of sodium dodecylbenzenesulfonate were dissolved in ion-exchange water to prepare 6250 g of liquid. As an oil phase, 29.1 wt % of 4-vinylpyridine, 7.3 wt % of styrene, 43.6 wt % of a blend of divinylbenzene and ethylvinylbenzene (ratio of divinylbenzene: 55 wt %), and 20 wt % of isooctane were blended to prepare 3750 g of liquid. Into the oil phase 1.2 wt % of benzoyl peroxide was dissolved, and fed to a 10 L reactor with a jacket for suspension blending. Subsequently, the water phase was fed to the reactor from the bottom and mildly stirred until oil droplets were uniformly dispersed. Then, warm water was flowed around the jacket to raise and keep the temperature at 60° C. for 2 hours and continuously at 90° C. for 4 hours. Subsequently, the temperature was cooled to room temperature, and solid-liquid separation was performed by filtration to recover the resin. After the recovered resin was extraction-cleaned with solvent to remove porous material, sieve classification was performed to produce a resin having a molar ratio of styrene/4-vinylbenzene of 1/4.0 and a degree of cross-linkage of 30%. The produced resin was dried and specific surface thereof was measured by BET method with AUTOSORB-1 (manufactured by Yuasa-ionics Company). The resin had a specific surface of 70 m$^2$/g, a pore volume of 0.24 ml/g, and an average pore diameter of 13.9 nm.

[Sulfonation Process of the Resin]

Into a separable flask with a mixer and a cooler, 0.2 g of silver sulfate and 150 ml of concentrated sulfuric acid was fed and heated to a temperature of 80° C. to 90° C. Then, 20 g of the prepared resin (dry basis) moistened with water was fed into a three-neck flask in split portions several times slowly. Subsequently, after the temperature was kept at 100° C. for 3 hours and cooled to room temperature, the content of the separable flask was slowly fed into 500 ml of cold water and filtered with a column filled with quartz wool. Furthermore, after sufficient cleaning with pure water, methanol cleaning was performed to produce a sulfonated resin. Into a glass column, 100 ml of the produced resin was filled and after passing of 500 ml of 2 N HCl, 250 ml of desalted water was passed for regeneration and water washing. Furthermore, 250 ml of 5% sodium chloride aqueous solution was passed through the resin to recover the eluent. The produced eluent was titrated with 1 N NaOH. The total cation exchange capacity of this resin was 1.15 mmol/ml.

Synthesis Example 2

A resin was prepared and sulfonation process was performed as in Synthesis example 1, except that, in the oil phase, 36.4 wt % of 4-vinylpyridine, 13.6 wt % of styrene, 30.0 wt % of a blend of divinylbenzene and ethylvinylbenzene (ratio of divinylbenzene: 80 wt %), and 20 wt % of isooctane were used.

The produced resin had a molar ratio of styrene/4-vinylbenzene of 1/2.7, and a degree of cross-linkage of 30%. The produced resin was dried prior to sulfonation process and specific surface thereof was measured by BET method with AUTOSORB-1 (manufactured by Yuasa-ionics Company). The resin had a specific surface of 55 m$^2$/g, a pore volume of 0.26 ml/g, and an average pore diameter of 19.1 nm. The total cation exchange capacity of the sulfonated resin was 1.37 mmol/ml.

Synthesis Example 3

A resin was prepared and sulfonation process was performed as in Synthesis example 1, except that, in the oil phase, 36.4 wt % of 4-vinylpyridine, 7.3 wt % of styrene, 20.4 wt % of a blend of divinylbenzene and ethylvinylbenzene (ratio of divinylbenzene: 55 wt %), and 20 wt % of isooctane were used.

The produced resin had a molar ratio of styrene/4-vinylbenzene of 1/5.0, and a degree of cross-linkage of 30%. The produced resin was dried prior to sulfonation process and specific surface thereof was measured by BET method with AUTOSORB-1 (manufactured by Yuasa-ionics Company). The resin had a specific surface of 57 m$^2$/g, a pore volume of 0.28 ml/g, and an average pore diameter of 20.0 nm. The total cation exchange capacity of the sulfonated resin was 1.18 mmol/ml.

Synthesis Example 4

A resin was prepared as in Synthesis example 1, except that, in the oil phase, 36.4 wt % of 4-vinylpyridine, 43.6wt % of a blend of divinylbenzene and ethylvinylbenzene (ratio of divinylbenzene: 55 wt %), and 20 wt % of isooctane were used.

The produced resin contained no styrene, and had a degree of cross-linkage of 30%. The produced resin was dried and specific surface thereof was measured by BET method with AUTOSORB-1 (manufactured by Yuasa-ionics Company). The resin had a specific surface of 67 m$^2$/g, a pore volume of 0.27 ml/g, and an average pore diameter of 15.8 nm.

[Experiment on Carbonylation Reaction]

On dry basis, 8.5 g of each of the resins in Synthesis examples 1 to 3 after sulfonation process, the resins in Synthesis examples 1 to 3 without sulfonation process, and the resin in Synthesis example 4, 0.197 g of rhodium acetate, and reaction liquid (25 g of methanol, 17.2 g of methyl iodide, and 37.5 g of acetic acid) were fed to a 200 ml autoclave made of zirconium for the reaction to proceed, producing a catalyst at a reaction temperature of 180° C., under a CO pressure of 5.0 MPaG for 1 hour. The amount of Rh supported in the catalyst was 0.85 wt %.

The total amount of the catalyst and the reaction liquid (20 g of methanol, 50 g of acetic acid, and 10 g of methyl iodide) were fed to a 200 ml autoclave made of zirconium for the reaction to proceed at a reaction temperature of 180° C., under a CO pressure of 5.0 MPaG for 1 hour.

Furthermore, regarding the resin in Synthesis example 4, 10% of a cation-exchange resin (Amberlyst-15) was further added to the autoclave for the reaction to proceed similarly.

Figure 2A:
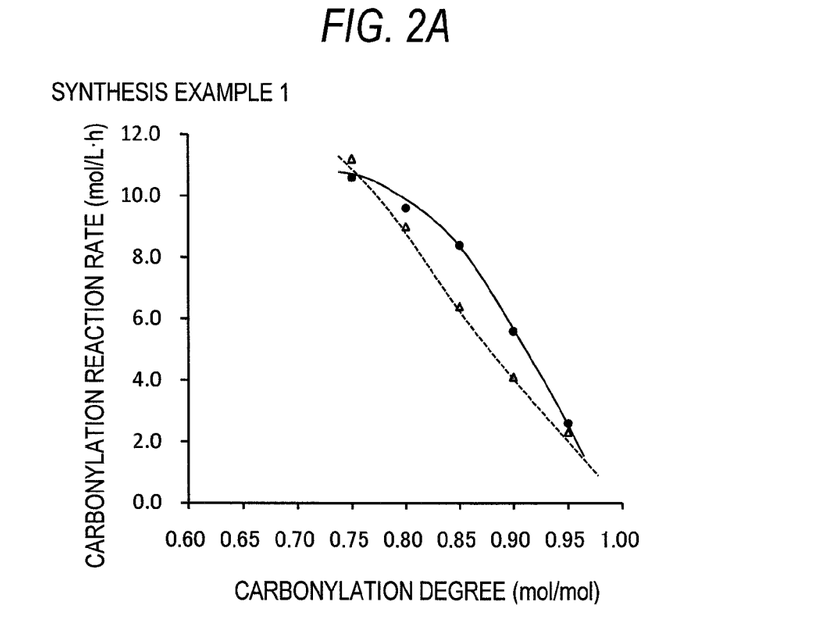
FIG. 2A is a graph illustrating difference in carbonylation reaction rate versus carbonylation degree between resins in Synthesis example 1 with and without providing acidic centers, in Example 1.
Figure 2B:
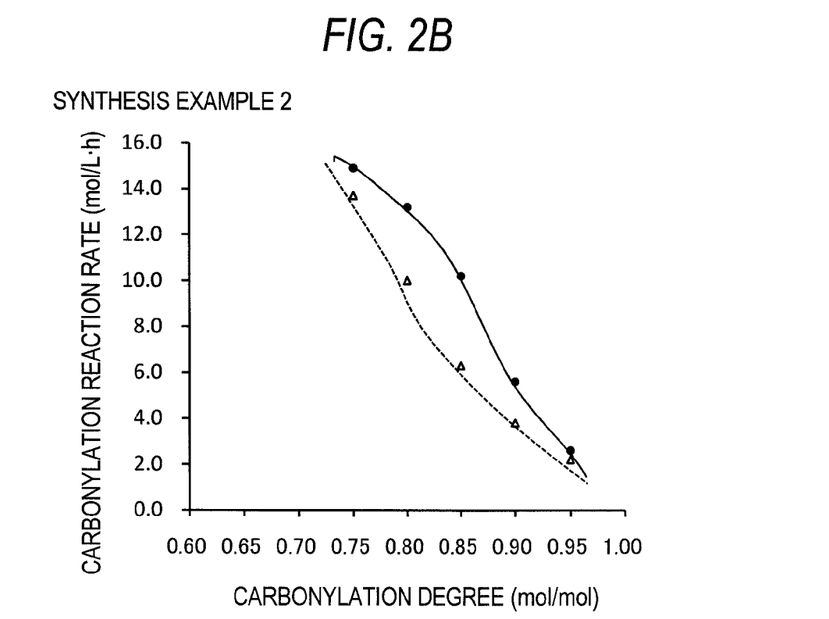
FIG. 2B is a graph illustrating difference in carbonylation reaction rate versus carbonylation degree between resins in Synthesis example 2 with and without providing acidic centers, in Example 1.
Figure 2C:
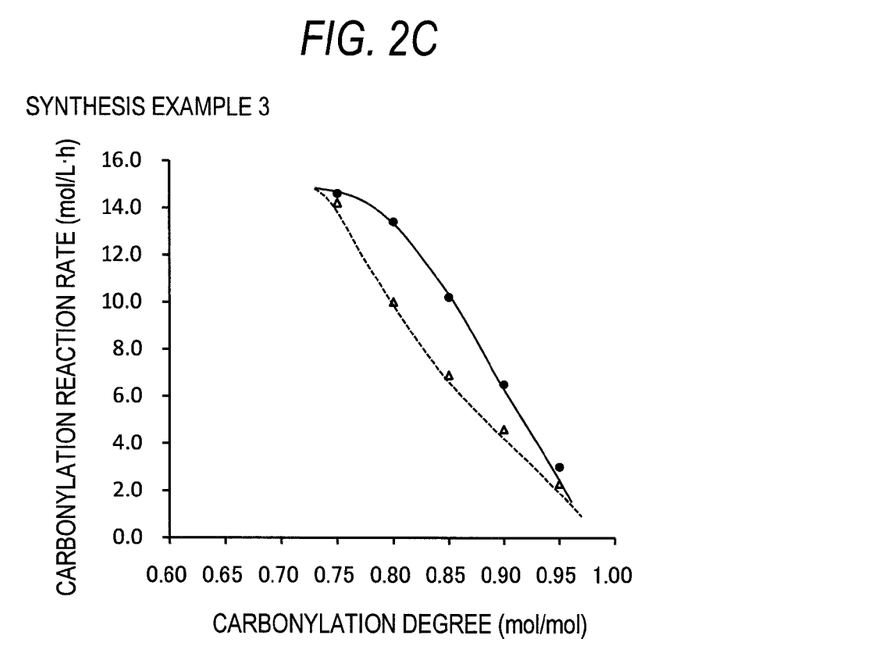
FIG. 2C is a graph illustrating difference in carbonylation reaction rate versus carbonylation degree between resins in Synthesis example 3 with and without providing acidic centers, in Example 1.
Figure 2D:
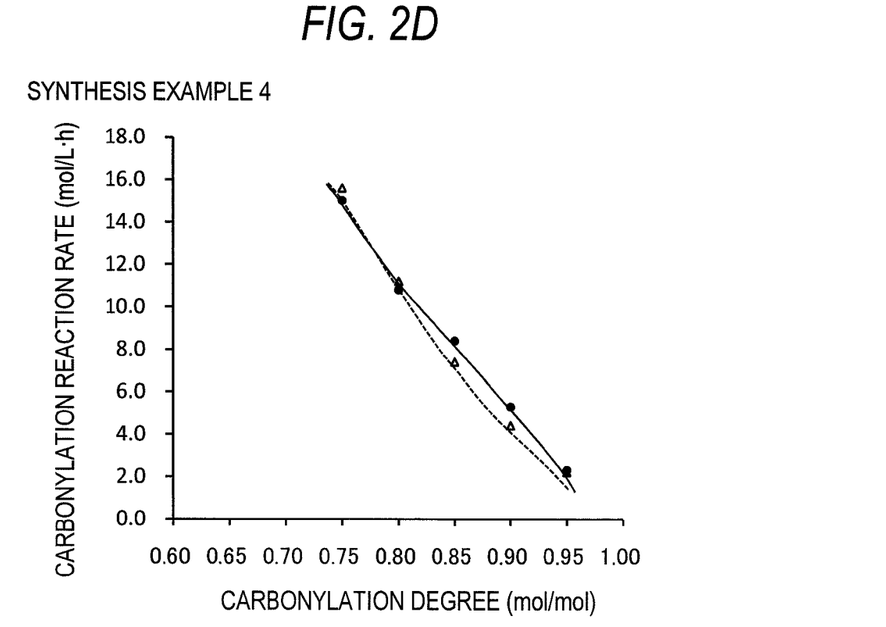
FIG. 2D is a graph illustrating difference in carbonylation reaction rate versus carbonylation degree between resins in Synthesis example 4 with and without addition of a cation-exchange resin, in Example 1.

In Table 3, carbonylation reaction rates obtained by the measurement of CO consumption rates for the reactions at different carbonylation degrees are shown. Each of the reaction rate ratios shown in Table 3 is calculated assuming the reaction rate with the resin in Synthesis example 4 without adding a cation-exchange resin as 1. In FIG. 2A for the resin in Synthesis example 1, in FIG. 2B for the resin in Synthesis example 2, in FIG. 2C for the resin in Synthesis example 3, and in FIG. 2D for the resin in Synthesis example 4, comparisons of carbonylation reaction rates at different carbonylation degrees between resins with providing acidic centers (solid line) and without providing acidic centers (dotted line) are shown, respectively.

As shown in Table 3 and FIG. 2A, FIG. 2B, FIG. 2C, and FIG. 2D, all the resins had an enhanced carbonylation rate in the region with a high carbonylation degree (Ca>0.8 mol/mol) with acidic centers provided compared to the conventional one (without providing acidic centers in Synthesis example 4). In addition, as is clear from FIG. 2A, FIG. 2B, FIG. 2C, and FIG. 2D, the carbonylation reaction rate was more significantly enhanced in the case that the pyridine resin was provided with acidic centers compared to the case that the reaction liquid was provided with acidic centers.

Example 2

On dry basis, 8.5 g of vinylpyridine resin, 0.197 g of rhodium acetate, and reaction liquid (25 g of methanol, 17.2 g of methyl iodide, and 37.5 g of acetic acid) were fed to a 200 ml autoclave made of zirconium for the reaction to proceed, producing a catalyst at a reaction temperature of 180° C., under a CO pressure of 5.0 MPaG for 1 hour. The amount of Rh supported in the catalyst was 0.85 wt %.

The total amount of catalyst and the reaction liquid (20 g of methanol, 50 g of acetic acid, and 10 g of methyl iodide) were fed to a 200 ml autoclave made of zirconium for the reaction to proceed at a reaction temperature of 180° C., under a CO pressure of 5.0 MPaG for 1 hour.

Figure 3:
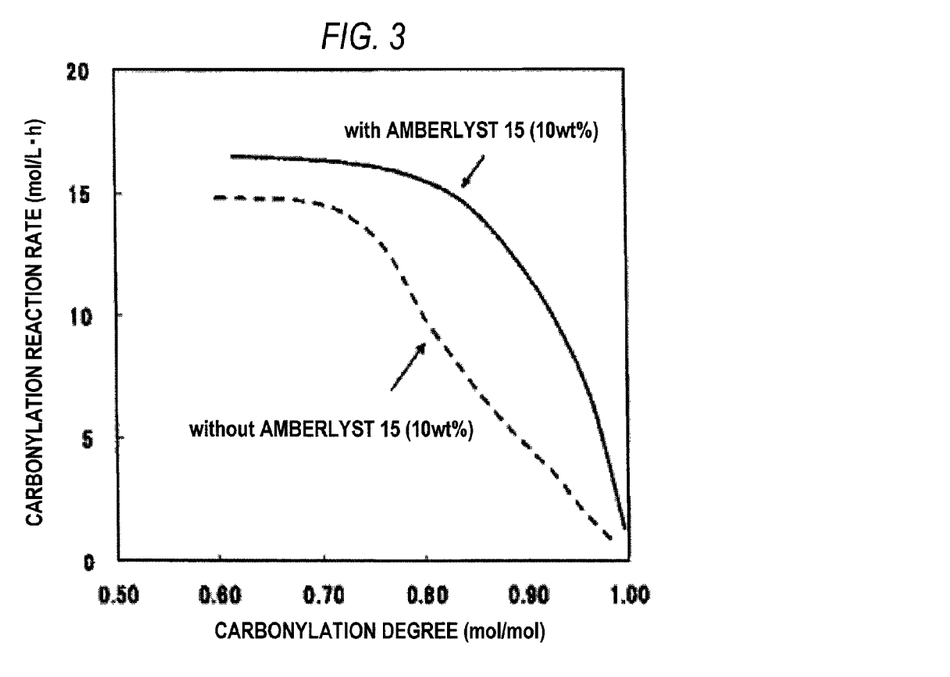
FIG. 3 is a graph illustrating difference in carbonylation reaction rate versus carbonylation degree between cases with and without addition of Amberlyst-15, in Example 2.

In FIG. 3, the relations between carbonylation degree and carbonylation reaction rate in the case that 10 wt % of Amberlyst-15 (manufactured by Rohm and Haas Company) as cation-exchange resin was added to the reaction liquid are shown. With addition of 10 wt % of the cation-exchange resin, significant increase of the reaction rate was observed particularly at a high carbonylation degree.

In Table 4, the results in the case that Amberlyst-31 (gel type) or Amberlyst-35 (MR type) was added are shown. It was found that either cation-exchange resin had nearly the same effects as Amberlyst-15.

TABLE 3

|  | Synthesis example 1 | | Synthesis example 2 | | Synthesis example 3 | | Synthesis example 4 | |
| --- | --- | --- | --- | --- | --- | --- | --- | --- |
| 4-vinylpyridine (wt %) | 36.4 | | 45.4 | | 45.5 | | 45.4 | |
| Styrene (wt %) | 9.1 | | 17.0 | | 9.0 | | — | |
| Molar ratio of 4-VP to styrene (—) | 4:1 | | 2.7:1 | | 5:1 | | — | |
| Acetic centers | Presence | Absence | Presence | Absence | Presence | Absence | Presence | Absence |
| Carbonylation degree (mol/mol) | Relative carbonylation reaction rate | | | | | | | |
| 0.75 | 0.68 | 0.72 | 0.96 | 0.88 | 0.94 | 0.91 | 0.96 | 1.00 |
| 0.80 | 0.86 | 0.80 | 1.18 | 0.89 | 1.20 | 0.89 | 0.96 | 1.00 |
| 0.85 | 1.14 | 0.86 | 1.38 | 0.85 | 1.38 | 0.93 | 1.14 | 1.00 |
| 0.90 | 1.27 | 0.93 | 1.27 | 0.86 | 1.48 | 1.05 | 1.20 | 1.00 |
| 0.95 | 1.18 | 1.05 | 1.18 | 1.00 | 1.36 | 1.05 | 1.05 | 1.00 |

TABLE 4

| Cation-exchange resin | Functional group | Total exchange capacity (mg equivalence/g) | Loading (wt %) | Carbonylation reaction rate (mol/L · h) | | |
| --- | --- | --- | --- | --- | --- | --- |
| | | | | Ca = 0.7 | Ca = 0.8 | Ca = 0.9 |
| Amberlyst15 (MR type) | —SO$_3$H | 4.7 | 1.0 | 14.2 | 10.8 | 5.0 |
| | | | 2.0 | 14.4 | 11.0 | 5.7 |
| | | | 6.0 | 15.2 | 12.5 | 8.2 |
| | | | 10.0 | 16.3 | 15.1 | 11.8 |
| Amberlyst31 (Gel type) | —SO$_3$H | 4.8 | 6.0 | 15.2 | 14.6 | 8.5 |
| Amberlyst35 (MR type) | —SO$_3$H | 5.2 | 6.0 | 15.5 | 13.6 | 8.5 |
| No addition | | | | 14.0 | 10.0 | 4.2 |

Example 3

In order to investigate the relations between the loading of cation-exchange resin and reaction rate, in Example 1, carbonylation reaction rates in the region at a carbonylation degree of 9.0 mol/mol were compared with variations in loading of Amberlyst-15 for use.

Figure 4:
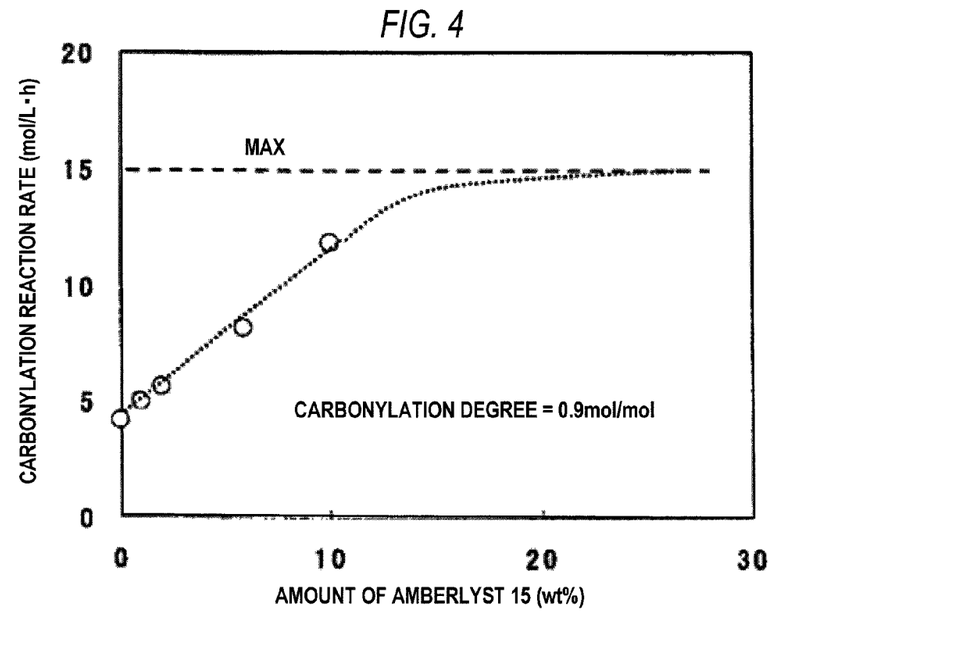
FIG. 4 is a graph illustrating changes in carbonylation reaction rate with variations in loading of Amberlyst-15, in Example 3.

The results are shown in FIG. 4. In the case that 10 wt % or more of $H_2O$ was added under this conditions (when hydrolysis of methyl acetate is not rate determining step), the space time yield was about 15 mol/L·h. It was found that in the case that the loading of Amberlyst-15 approached 30%, the carbonylation reaction rate also approached this space time yield.

Example 4

In order to study effects of acids other than cation-exchange resins, the relations between carbonylation degree and carbonylation reaction rate were investigated by adding 2 wt % of sulfuric acid or 4 wt % of p-toluenesulfonic acid instead of Amberlyst-15 used in Example 1. The experiments were performed under the same conditions as in Example 1 except for the added acid.

The results are shown in Table 5. It was verified that the addition of sulfuric acid or p-toluenesulfonic acid significantly enhanced the reaction rate in the region at a high carbonylation degree, as well as cation-exchange resins.

TABLE 5

| Added acid | Loading (wt %) | Carbonylation reaction rate (mol/L · h) | | |
|---|---|---|---|---|
| | | Ca = 0.7 | Ca = 0.8 | Ca = 0.9 |
| Sulfuric acid | 2.0 | 15.8 | 14.0 | 10.6 |
| p-Toluenesulfonic acid | 4.0 | 15.1 | 12.5 | 7.9 |
| No addition | | 14.0 | 10.0 | 4.2 |

This application claims the benefit of Japanese Patent Application No. 2010-026293, filed Feb. 9, 2010, which is hereby incorporated by reference herein in its entirety.

The invention claimed is:

1. A method for producing acetic acid by heterogeneous carbonylation of methanol with carbon monoxide in a reaction liquid in the presence of alkyl iodide and a solid catalyst containing rhodium and including hydrolysis of methyl acetate, wherein the hydrolysis of the methyl acetate is accelerated by an acid having an acid dissociation constant ($pK_a$) smaller than the constant of acetic acid, that acid being co-existent with the solid catalyst in the reaction system;

wherein the carbonylation of methanol is performed in a region where liquid reaction product has a carbonylation degree Ca not lower than 0.7 mol/mol; and wherein the rhodium is supported on a carrier comprising a sulfonated copolymer of 4-vinylpyridine, styrene, and divinylbenzene.

2. The method for producing acetic acid according to claim 1, wherein the copolymer comprises 5% to 60% by weight of 4-vinylpyridine, 1% to 50% by weight of styrene, and 5% to 40% by weight of divinylbenzene.

3. The method for producing acetic acid according to claim 1, wherein a strong acidic cation-exchange resin is added to the reaction liquid.

4. The method for producing acetic acid according to claim 3, wherein the cation-exchange resin is added in the amount of 1 wt % to 30 wt % of the reaction liquid.

* * * * *